United States Patent
Matsuzaki et al.

(10) Patent No.: US 8,071,053 B2
(45) Date of Patent: Dec. 6, 2011

(54) DISPENSING APPARATUS

(75) Inventors: Shunji Matsuzaki, Kanagawa (JP); Katsunori Hirata, Kanagawa (JP)

(73) Assignee: A & T Corporation, Fujisawa-shi (JP)

( * ) Notice: Subject to any disclaimer, the term of this patent is extended or adjusted under 35 U.S.C. 154(b) by 659 days.

(21) Appl. No.: 12/162,710

(22) PCT Filed: Mar. 27, 2007

(86) PCT No.: PCT/JP2007/056378
§ 371 (c)(1),
(2), (4) Date: Jul. 30, 2008

(87) PCT Pub. No.: WO2007/114117
PCT Pub. Date: Oct. 11, 2007

(65) Prior Publication Data
US 2009/0038415 A1 Feb. 12, 2009

(30) Foreign Application Priority Data
Apr. 6, 2006 (JP) ................... 2006-105483

(51) Int. Cl.
*G01N 35/10* (2006.01)
(52) U.S. Cl. .......... 422/509; 422/502; 422/64; 436/180; 73/864.25
(58) Field of Classification Search .......... None
See application file for complete search history.

(56) References Cited

U.S. PATENT DOCUMENTS
4,276,260 A * 6/1981 Drbal et al. ............... 422/510
4,311,667 A * 1/1982 Gocho ............... 422/64

FOREIGN PATENT DOCUMENTS
| | | |
|---|---|---|
| JP | 57-61954 | 4/1982 |
| JP | 1-24630 | 7/1989 |
| JP | 2-311764 | 12/1990 |
| JP | 9-21815 | 1/1997 |
| JP | 2000-38216 | 2/2000 |
| JP | 2002-311036 A1 | 10/2002 |

OTHER PUBLICATIONS
International Search Report for International Application No. PCT/JP2007/056378 dated May 21, 2007 (4 Sheets total, including reference JP 57-21468 corrected to JP 57-61954).

* cited by examiner

*Primary Examiner* — P. Kathryn Wright
(74) *Attorney, Agent, or Firm* — Kratz, Quintos & Hanson, LLP

(57) ABSTRACT

A dispensing apparatus includes a dispensing arm, a driving motor, and a transmitting/buffering unit. The dispensing arm is rotatable and conveys a fluid drawn at a predetermined drawing position to a predetermined discharge position. The driving motor rotates the dispensing arm. The transmitting/buffering unit includes a crank shaft that rotates through a driving force of the driving motor and a crank rod that is coupled with the crank shaft and rotates with a rotation of the crank shaft thereby rotating the dispensing arm.

6 Claims, 13 Drawing Sheets

RELATED ART FIG.19
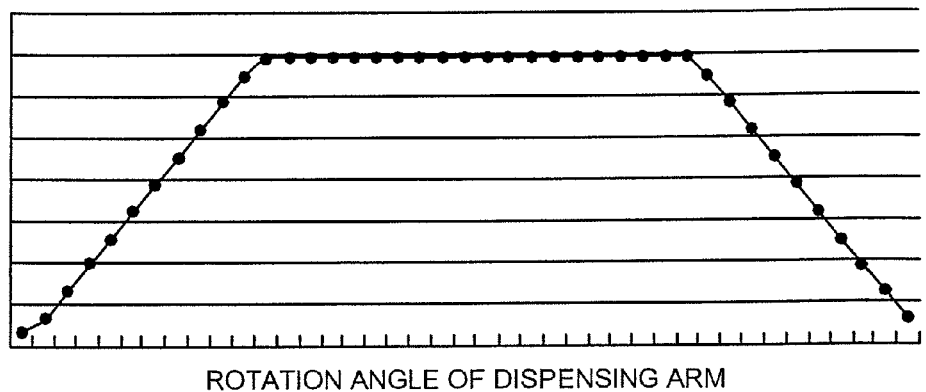
RELATED ART FIG.20
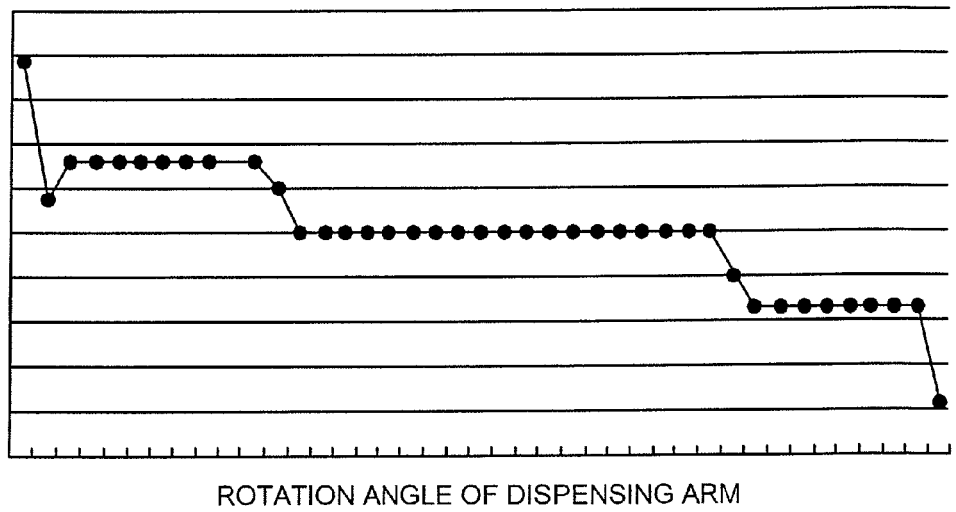

1

DISPENSING APPARATUS

TECHNICAL FIELD

The present invention relates to a dispensing apparatus that conveys a fluid drawn at a predetermined drawing position to a predetermined discharge position by rotating a dispensing arm, and more particularly to a dispensing apparatus that rotates a dispensing arm through a driving force of a motor.

BACKGROUND ART

In an auto analyzer used in, for example, clinical tests, a dispensing apparatus that can dispense a reagent with respect to a specimen to generate a chemical-reaction fluid of the specimen and the reagent is conventionally used. For example, in a multi-allergen test used to identify an allergy of a patient, when the dispensing apparatus dispenses a reagent (a biotinylated allergen) with respect to a specimen (blood) from a patient, a chemical-reaction fluid including a material (a specific IgE antibody conjugate) used for auto analysis can be generated.

Among such dispensing apparatuses, as shown in later-explained FIG. 18, is a dispensing apparatus that draws, by a dispensing nozzle provided at a distal end of a dispensing arm capable of rotating, a reagent from a reagent container held on a reagent table, rotates the dispensing arm driven by a stepping motor to move the dispensing nozzle onto a carriage table, and discharges the reagent into a specimen container held on the carriage table, thereby dispensing the reagent with respect to the specimen (see, e.g., Patent Document 1).

FIG. 18 is a perspective view of an appearance of a conventional dispensing apparatus 1800 utilizing the conventional technology. The conventional dispensing apparatus 1800 is an apparatus that discharges a reagent 1852 drawn from a reagent container 1851 arranged in a reagent table 1850 into a specimen container 1861 that is arranged in a specimen table 1860 and holds a specimen 1862. This dispensing apparatus 1800 includes a case 1801, a dispensing arm 1810, a driving motor 1820, a driving transmission unit 1830, and a drawing/discharging unit 1840.

The dispensing arm 1810 and the driving transmission unit 1830 are provided on an upper portion of the case 1801, and the driving motor 1820 is enclosed in the case. The dispensing arm 1810 includes a dispensing arm shaft 1811 and an arm 1812 and rotates driven by the driving motor 1820.

The dispensing arm shaft 1811 has a rotatable, rod-like shape and is assembled on an upper portion of the case 1801. The dispensing arm shaft 1811 axially supports the arm 1812 and rotates together with the arm 1812 driven by the driving motor 1820. The dispensing arm shaft 1811 moves up and down by a driving mechanism (e.g., a motor or a hydraulic cylinder) controlled by a non-depicted computer.

The arm 1812 has a rod-like shape that is pivotally supported by the dispensing arm shaft 1811 and rotates together with the dispensing arm shaft 1811, and a dispensing nozzle 1843 is held at a distal end of the arm 1812. When the arm 1812 rotates together with the dispensing arm shaft 1811 driven by the driving motor 1820, the dispensing nozzle 1843 held at the distal end of the arm 1812 can be reciprocated between a predetermined drawing position and a predetermined discharge position.

When the arm 1812 moves up and down together with the dispensing arm shaft 1811 by a driving mechanism controlled by the non-depicted computer, the dispensing nozzle 1843 held at the distal end of the arm 1812 can be moved up and down. For example, when the dispensing nozzle 1843 is positioned at the predetermined drawing position (immediately above the reagent container 1851) to draw the reagent 1852 from the reagent container 1851 arranged in the reagent table 1850, moving the arm 1812 down together with the dispensing arm shaft 1811 enables insertion of a distal end of the dispensing nozzle 1843 into the reagent 1852 in the reagent container 1851.

The driving motor 1820 is a stepping motor driven under the control of the non-depicted computer to rotate the dispensing arm 1810 through the driving transmission unit 1830. The driving transmission unit 1830 includes a drive shaft, a driving pulley, and a driving belt, and transmits driving force of the driving motor 1820 to the dispensing arm 1810.

The drawing/discharging unit 1840 includes a syringe pump unit 1841, a syringe pump pipe 1842, and a dispensing nozzle 1843. The syringe pump unit 1841 generates a pressure (a negative pressure) that is used to draw the reagent 1852 and a pressure (a positive pressure) that is used to discharge the reagent 1852 under the control of the non-depicted computer.

The pressures (the negative pressure and the positive pressure) generated by the syringe pump unit 1841 are transmitted to the dispensing nozzle 1843 through the syringe pump pipe 1842, and for example, the generation of a pressure (the negative pressure) by the syringe pump unit 1841 when the distal end of the dispensing nozzle 1843 is inserted in the reagent 1852 in the reagent container 1851 enables drawing the reagent 1852 in the reagent container 1851 from the distal end of the dispensing nozzle 1843.

On the contrary, the generation of a pressure (a positive pressure) by the syringe pump unit 1841 when the distal end of the dispensing nozzle 1843 having the reagent 1852 sucked therein is inserted in the specimen container 1861 enables discharge of the reagent 1852 with respect to the specimen container 1861 from the distal end of the dispensing nozzle 1843.

Patent Document 1: Japanese patent Application Laid-open No. 2002-311036

DISCLOSURE OF INVENTION

Problem to be Solved by the Invention

However, in the conventional technology, for example, when the dispensing arm starts rotating or when the dispensing arm stops rotating, a rotational speed of the dispensing arm suddenly changes or a sudden change (a so-called impact shock) in inertial load occurs in the dispensing arm because of the driving characteristics of the motor that drives the dispensing arm.

FIG. 19 is a graph of an example of a change in the rotational speed of the dispensing arm 1810 in the conventional dispending apparatus 1800 utilizing conventional technology. As shown in FIG. 19, an ordinate represents a rotational speed of the dispensing arm 1810, and an abscissa represents a rotation angle of the dispensing arm 1810. As shown in FIG. 19, a rotational speed of the dispending arm 1810 is precipitously increased to reach a maximum value immediately after the dispensing arm 1810 starts rotating.

Then, the maximum rotational speed of the dispensing arm 1810 is maintained. The rotational speed of the dispensing arm is precipitously reduced immediately before the dispending arm 1810 stops rotating until the dispensing arm 1810 stops rotating. As shown in FIG. 19, the rotational speed of the dispensing arm 1810 is precipitously changed when the dispending arm 1810 starts rotating and when the dispending arm 1810 stops rotating.

FIG. 20 is a graph of an example of a change in inertial load generated in the dispending arm 1810 in the conventional dispending apparatus 1800 utilizing conventional technology. As shown in FIG. 20, an ordinate represents an inertial load generated in the dispending arm 1810 and an abscissa represents a rotation angle of the dispending arm 1810.

As shown in FIG. 20, an inertial load generated in the dispensing arm 1810 precipitously changes immediately after rotation of the dispensing arm 1810 is started, immediately before the rotational speed of the dispensing arm 1810 becomes maximum, immediately after a reduction in the rotational speed of the dispensing arm 1810 is started, and immediately before rotation of the dispensing arm 1810 is stopped.

Therefore, as a dispensing volume of the reagent is extremely small (2 to 200 microliters) and precision with the dispensing volume is required, a problem occurs in that the reagent drawn in the dispensing nozzle provided at the distal end of the dispensing arm is dispersed around the dispensing arm reducing dispensing precision.

To solve the problem in the conventional technology, it is an object of the present invention to provide a dispensing apparatus that can convey a fluid drawn by a dispensing nozzle provided at a distal end of a dispensing arm at a predetermined drawing position to a predetermined discharge position without dispersion and can improve a dispensing precision.

Means for Solving Problem

To solve the problems above and achieve an object, a dispensing apparatus according to the invention of claim 1 includes a dispensing arm that is rotatable and conveys a fluid drawn by a dispensing nozzle held at a distal end and drawn at a predetermined drawing position to a predetermined discharge position; a driving motor that rotates the dispensing arm; and a transmission unit including a crank shaft that rotates through a driving force of the driving motor and a crank rod that is coupled with the crank shaft, rotates through rotation of the crank shaft thereby rotating the dispending arm.

A dispensing apparatus according to the invention of claim 2, based on the invention of claim 1, is characterized by the transmission unit coupling the crank shaft with the crank rod so that a variation in rotation angle of the dispensing arm becomes small when the dispensing arm starts rotating from the predetermined drawing position and when the dispensing arm stops rotating at the predetermined discharge position.

A dispensing apparatus according to the invention of claim 3, based on the invention of claim 1, further is characterized by the transmission unit including the crank shaft that rotates through a driving force of the driving motor, a crank rod slider that is capable of rotating interlocked with rotation of the dispensing arm and has a through hole in which one end of the crank rod is inserted and fitted, a crank lever that is coupled with the crank shaft and rotates with a rotation of the crank shaft, and a crank rod that has one end slidably inserted and fitted in the through hole formed in the crank rod slider and another end coupled with the crank lever by the crank pin, and rotates around a rotating shaft of the crank rod slider to rotate the crank rod slider.

A dispensing apparatus according to the invention of claim 4, based on the invention of claim 1, further includes a drawing/discharging unit that draws and discharges the fluid, and is mounted on the dispensing arm.

A dispensing apparatus according to the invention of claim 5, based on the invention of any one of claims 1 to 4, further includes an extending/retracting unit that extends and retracts the dispensing arm to move the dispensing nozzle held at the distal end of the dispensing arm along an extending direction of the dispensing arm.

A dispensing apparatus according to the invention of claim 6, based on the invention of claim 5, is characterized by the extending/retracting unit including a second driving motor that extends and retracts the dispensing arm; and a second transmission unit that includes a second crank shaft that rotates through a driving force of the second driving motor, and a second crank rod that is coupled with the second crank shaft, rotates through rotation of the second crank shaft thereby extending and retracting the dispensing arm.

A dispensing apparatus according to the invention of claim 7, based on the invention of claim 6, is characterized the second transmission unit coupling the second crank shaft with the second crank rod so that a variation in extending/retracting speed of the dispensing arm becomes small when the dispensing arm starts extension and retraction, and when the dispensing arm stops extension and retraction.

A dispensing apparatus according to the invention of claim 8, based on the invention of claim 6 or 7, is characterized by the second transmission unit including a second crank shaft that rotates through a driving force of the second driving motor; a second crank lever that is coupled with the second crank shaft and rotates with rotation of the second crank shaft; and a second crank rod that has one end coupled with the second crank lever by the second crank pin and the other end coupled with the dispensing arm by the piston pin, and rotates around the piston pin to extend and retract the dispensing arm.

Effect of the Invention

The present invention can demonstrate an effect of implementing a dispensing apparatus that can convey a fluid drawn by the dispensing nozzle provided at the distal end of the dispensing arm and drawn at the predetermined drawing position to the predetermined discharge position without dispersion and can improve dispensing precision.

BRIEF DESCRIPTION OF DRAWINGS

FIG. 19 is a graph of an example of a change in the rotational speed of a dispensing arm in the conventional dispending apparatus utilizing conventional technology; and FIG. 20 is a graph of an example of a change in inertial load generated in the dispending arm in the conventional dispending apparatus utilizing conventional technology.

Figure 1:
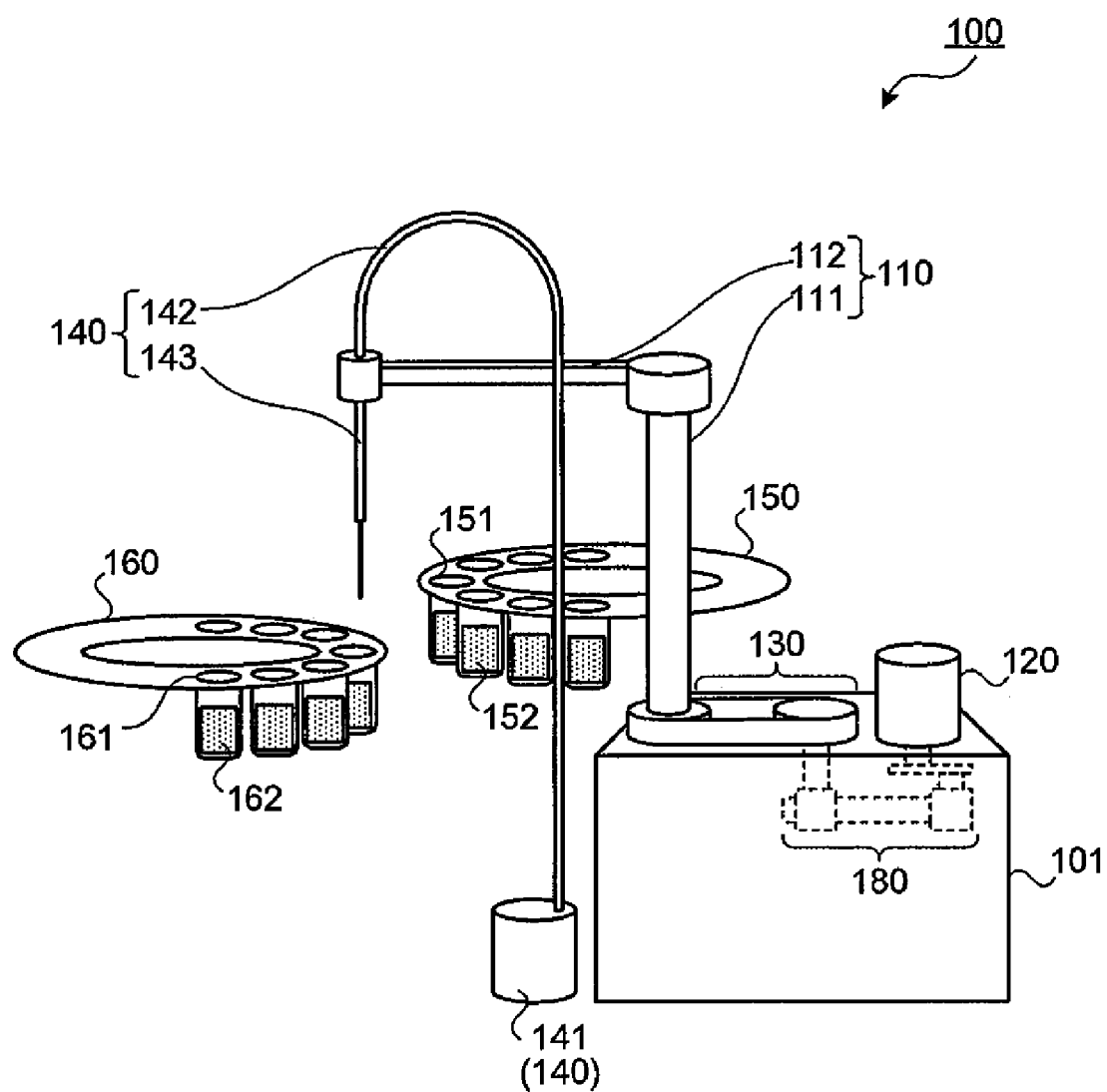
FIG. 1 is a perspective view of a dispensing apparatus according to a first embodiment of the present invention.

EXPLANATION OF LETTERS OR NUMERALS 100 dispensing apparatus
101 case
110 dispensing at n
111 dispensing arm shaft
112 arm
120 driving motor
130 driving transmission unit
131 drive shaft
132 driving pulley
133 driving belt
140 drawing/discharging unit
141 syringe pump unit
142 syringe pump pipe
143 dispensing nozzle
150 reagent table
151 reagent container
152 reagent
160 specimen table
161 specimen container
162 specimen
180 transmitting/buffering unit
181 crank lever
182 crank rod
183 crank rod slider
184 crank shaft
185 crank pin

BEST MODE(S) FOR CARRYING OUT THE INVENTION

Exemplary embodiments of a dispensing apparatus according to the present invention are explained hereinafter in detail with reference to the accompanying drawings.

First Embodiment

Structure of Dispensing Apparatus 100

First, a structure of a dispensing apparatus 100 according to the first embodiment is explained with reference to FIG. 1. FIG. 1 is a perspective view of the dispensing apparatus 100 according to the first embodiment of the present invention. As shown in FIG. 1, the dispensing apparatus 100 is an apparatus that discharges a reagent 152 drawn from a reagent container 151 arranged in a reagent table 150 into a specimen container 161 that is arranged in a specimen table 160 and holds a specimen 162 therein.

Although the dispensing apparatus 100 that dispenses the reagent 152 with respect to the specimen 162 is explained as an example, the present invention is not restricted thereto and, for example, the dispensing apparatus 100 dispenses a fluid and may dispense the specimen 162 with respect to the reagent 152.

The dispensing apparatus 100 includes a case 101, a dispensing arm 110, a driving motor 120, a driving transmission unit 130, a drawing/discharging unit 140, and a transmission/buffering unit 180, and unlike the conventional dispensing apparatus 1800, the dispensing arm 110 is rotated through the transmission/buffering unit 180 by a driving force of the driving motor 120.

The case 101 is of a rectangular shape, where the dispensing arm 110, the driving transmission unit 130, and the driving motor 120 are provided at an upper portion of the case 101, and the transmission/buffering unit 180 is enclosed in the case 101. The dispensing arm 110 includes a dispensing arm shaft 111 and an arm 112, and is rotated through a driving force of the driving motor 120.

The dispensing arm shaft 111 has a rod-like shape and is provided at an upper portion of the case 101 and such that a rotating motion is enabled. The dispensing arm shaft 111 is coupled with the arm 112 and rotates the arm 112 through a driving force the driving motor 120. The dispensing arm shaft 111 moves up and down by a driving mechanism (e.g., a motor or a hydraulic cylinder) controlled by a non-depicted computer.

The arm 112 has a rod-like shape that is coupled with the dispensing arm shaft 111 and rotates together with the dispensing arm shaft 111. A dispensing nozzle 143 is held at a distal end of the arm 112. When the arm 112 rotates together with the dispensing arm shaft 111 through a driving force of the driving motor 120, the dispensing nozzle 143 held at the distal end of the arm 112 can be reciprocated between a predetermined drawing position and a predetermined discharge position.

When the arm 112 moves up and down together with the dispensing arm shaft 111 through a driving force of the driving mechanism controlled by the non-depicted computer, the dispensing nozzle 143 held at the distal end of the arm 112 can be moved up and down. For example, when the dispensing nozzle 143 is positioned at the predetermined drawing position (immediately above the reagent container 151) to draw the reagent 152 from the reagent container 151 arranged in the reagent table 150, downward movement of the arm 112 together with the dispensing arm shaft 111 enables insertion of a distal end of the dispensing nozzle 143 into the reagent 152 in the reagent container 151.

The driving motor 120 is a motor (a direct-current motor or an alternating-current motor) that is driven under the control of the non-depicted computer to rotate the dispensing arm 110 through the driving transmission unit 130 and the transmission/buffering unit 180. The driving transmission unit 130 includes a drive shaft 131, a driving pulley 132, and a driving belt 133. The driving transmission unit 130 and the transmission/buffering unit 180 transmit a driving force of the driving motor 120 to the dispensing arm 110.

The drawing/discharging unit 140 includes a syringe pump unit 141, a syringe pump pipe 142, and the dispensing nozzle 143. The syringe pump unit 141 produces a pressure (a negative pressure) that is used to draw the reagent 152 and a pressure (a positive pressure) that is used to discharge the reagent 152 under the control of the non-depicted computer.

The pressures (the negative pressure and the positive pressure) generated by the syringe pump unit 141 are transmitted to the dispensing nozzle 143 through the syringe pump pipe 142 and, for example, when the distal end of the dispensing nozzle 143 is inserted in the reagent 152 in the reagent container 151, generation of the pressure (the negative pressure) by the syringe pump unit 141 enables drawing, from the distal end of the dispensing nozzle 143, the reagent 152 in the reagent container 151.

On the contrary, when the distal end of the dispensing nozzle 143 having the reagent 152 drawn therein is inserted in the specimen container 161, generation of the pressure (the positive pressure) by the syringe pump unit 141 enables discharge, from the distal end of the dispensing nozzle 143, of the reagent 152 with respect to the specimen container 161.

The transmission/buffering unit 180 and the driving transmission unit 130 transmit a driving force of the driving motor 120 to the dispensing arm 110. The transmission/buffering unit 180 absorbs a sudden change in rotational speed that occurs with the driving motor when driving of the driving motor 120 starts or when driving of the driving motor 120 stops, thereby alleviating a change in the rotational speed of the dispensing arm 110 that rotates through a driving force of the driving motor 120.

(Structure of Transmitting/Buffering Unit 180)

Figure 2:
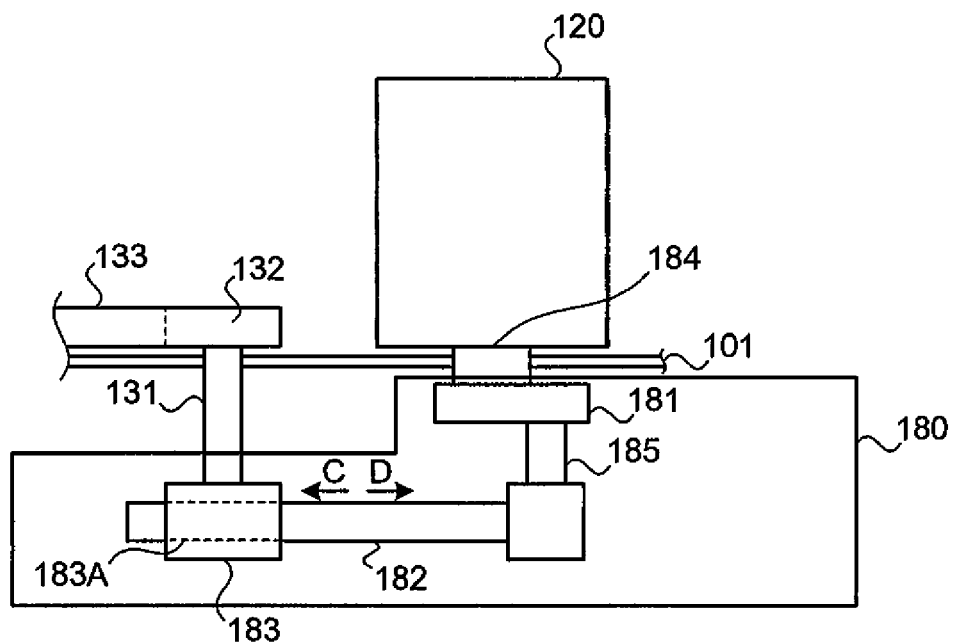
FIG. 2 is a side view of a transmission/buffering unit.
Figure 3:
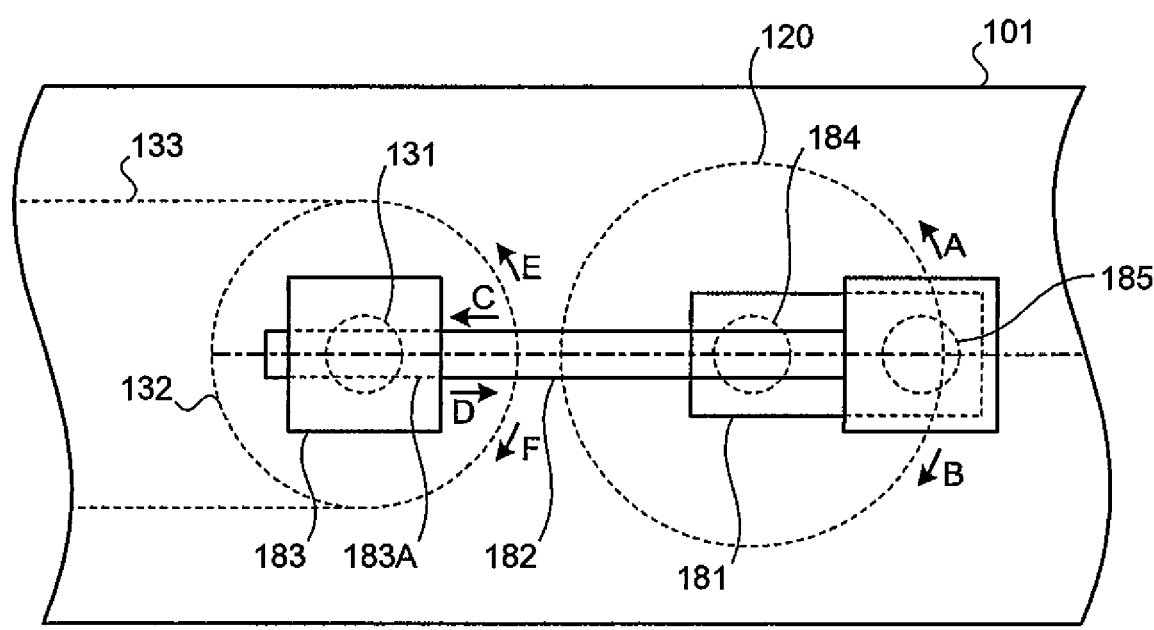
FIG. 3 is a plan view of the transmission/buffering unit.

Details of a structure of the transmission/buffering unit 180 are explained with reference to FIGS. 2 and 3. FIG. 2 is a side view of the transmission/buffering unit 180. FIG. 3 is a plan view of the transmission/buffering unit 180. As shown in FIGS. 2 and 3, the transmission/buffering unit 180 includes a crank lever 181, a crank rod 182, a crank rod slider 183, a crank shaft 184, and a crank pin 185.

The crank lever 181 converts a rotating motion of the crank shaft 184 generated through a driving force of the driving motor 120 into an oscillating motion of the crank rod 182, is coupled with the crank shaft 184, and rotates together with the crank shaft 184. The crank rod 182 is coupled with the crank lever 181 through the crank pin 185 provided at a distal end of the crank lever 181 to enable a rotating motion.

The crank lever 181, together with the crank shaft 184 through a driving force of the driving motor 120, can rotate the dispensing arm 110 in a rotational direction toward a predetermined discharge position (a direction A) and rotate the dispensing arm 110 in a rotational direction toward a predetermined drawing position (a direction B) and can rotate the crank rod 182 coupled thereto by the crank pin 185.

The crank rod 182 has a bar-like shape and couples the crank lever 181 with the crank rod slider 183 so that the crank rod slider 183 can rotate with rotation of the crank lever 181. One end of the crank rod 182 is inserted and fitted through a through hole 183A formed in the crank rod slider 183 and is slidable in a direction C and a direction D, and the other end thereof is coupled with the crank lever 181 by the crank pin 185.

The crank rod slider 183 is formed at an end portion of the drive shaft 131 included in the driving transmission unit 130 and rotates together with the drive shaft 131 and the pulley 132. The through hole 183A is formed in the crank rod slider 183, and the crank rod 182 is inserted and fitted in the through hole 183A to be slidable in the direction C and the direction D. The crank rod slider 183 rotates the dispensing arm 110 together with the drive shaft 131 in a rotational direction toward the predetermined discharge position (a direction E) and rotates the dispensing arm 110 in a rotational direction toward the predetermined drawing position (a direction F) through rotation of the crank rod 182 associated with rotation of the crank lever 181.

In the dispensing apparatus 100 according to this embodiment, a diameter of a driven part of the driving pulley 132 by the driving belt 133 is substantially equal to a diameter of a driven part of the dispensing arm 110 by the driving belt 133 so that a rotation angle of the crank rod slider 183 becomes substantially equal to a rotation angle of the dispensing arm 110, but the present invention is not restricted thereto, and the diameter of the driven part of the driving pulley 132 by the driving belt 133 may be different from the diameter of the driven part of the dispensing arm 110 by the driving belt 133 so that the rotation angle of the crank rod slider 183 becomes different from the rotation angle of the dispensing arm 110.

The crankshaft 184 rotates interlocked with a driving force of the driving motor 120. The crankshaft 184 is coupled with the crank lever 181. The crank lever 181 rotates together with the crankshaft 184 and is coupled with the crank rod 182 by the crank pin 185 allowing a rotating motion.

(State of Dispensing Apparatus 100 when Dispensing Nozzle 143 is Positioned at Predetermined Drawing Position)

Figure 4:
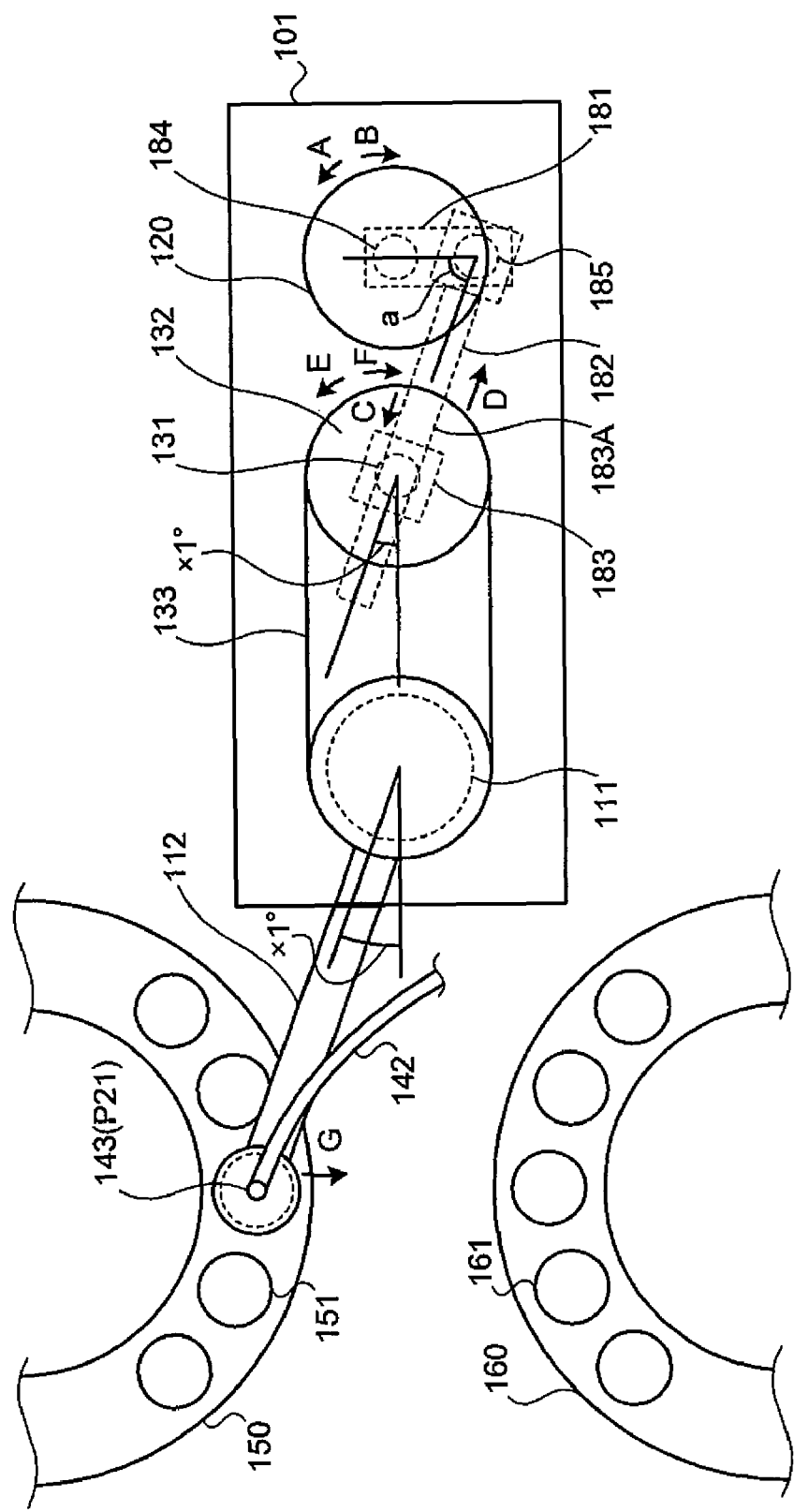
FIG. 4 is a plan view of the dispensing apparatus when a dispensing nozzle held at the distal end of a dispensing arm is positioned at the predetermined drawing position.

An operation of the thus configured dispensing apparatus 100 is explained with reference to FIGS. 4 to 8. First, a state of the dispensing apparatus 100 when the dispensing nozzle 143 is positioned at the predetermined drawing position is explained with reference to FIG. 4. FIG. 4 is a plan view of the dispensing apparatus 100 when the dispensing nozzle 143 held at the distal end of the dispensing arm 110 is positioned at the predetermined drawing position.

As shown in FIG. 4, under the control of the non-depicted computer, the driving motor 120 is stopped and rotation of the crank lever 181 that rotates through a driving force of the driving motor 120 is stopped in a state where the crank pin 185 that couples the crank lever 181 with the crank rod 182 is positioned at a position corresponding to the predetermined drawing position.

When the crank pin 185 that couples the crank lever 181 with the crank rod 182 is positioned at the position corresponding to the predetermined drawing position, an incline of $X1°$ occurs with respect to the crank rod 182 coupled with the crank pin 185 and the crank rod slider 183. At this time, an intersecting angle (an angle a) of the crank lever 181 and the crank rod 182 must fall within 90°, and 90° being the most desirable.

Here, in the dispensing apparatus 100 according to this embodiment, since the diameter of the driven part of the driving pulley 132 rotating together with the crank rod slider 183 by the driving belt 133 is substantially equal to the diameter of the driven part of the dispensing arm 110 by the driving belt 133, a rotation angle of the dispensing arm 110 is substantially equal to a rotation angle of the crank rod slider 183 (i.e., an incline angle of the crank rod 182).

Therefore, as shown in FIG. 4, the crank rod slider 183, the driving pulley 132, and the dispensing arm 110 rotate $X1°$ due to an occurrence of the incline of $X1°$ with respect to the crank rod 182, and the dispensing arm 110 inclines $X1°$. As a result, the dispensing nozzle 143 held at the distal end of the dispensing arm 110 becomes in a state of being positioned at the predetermined drawing position (P21).

In this manner, when the dispensing nozzle 143 is moved down together with the dispensing arm 110 from the state where the dispensing nozzle 143 is positioned at the predetermined drawing position (P21), the distal end of the dispensing nozzle 143 can be inserted into the reagent 152 in the reagent container 151. When the distal end of the dispensing nozzle 143 is inserted into the reagent 152 in the reagent container 151, generation of a pressure (a negative pressure) by the syringe pump unit 141 enables the reagent 152 in the reagent container 151 to be drawn from the distal end of the dispensing nozzle 143.

(Operation of Dispensing Apparatus 100 when Dispensing Arm 110 Starts Rotating)

Figure 5:
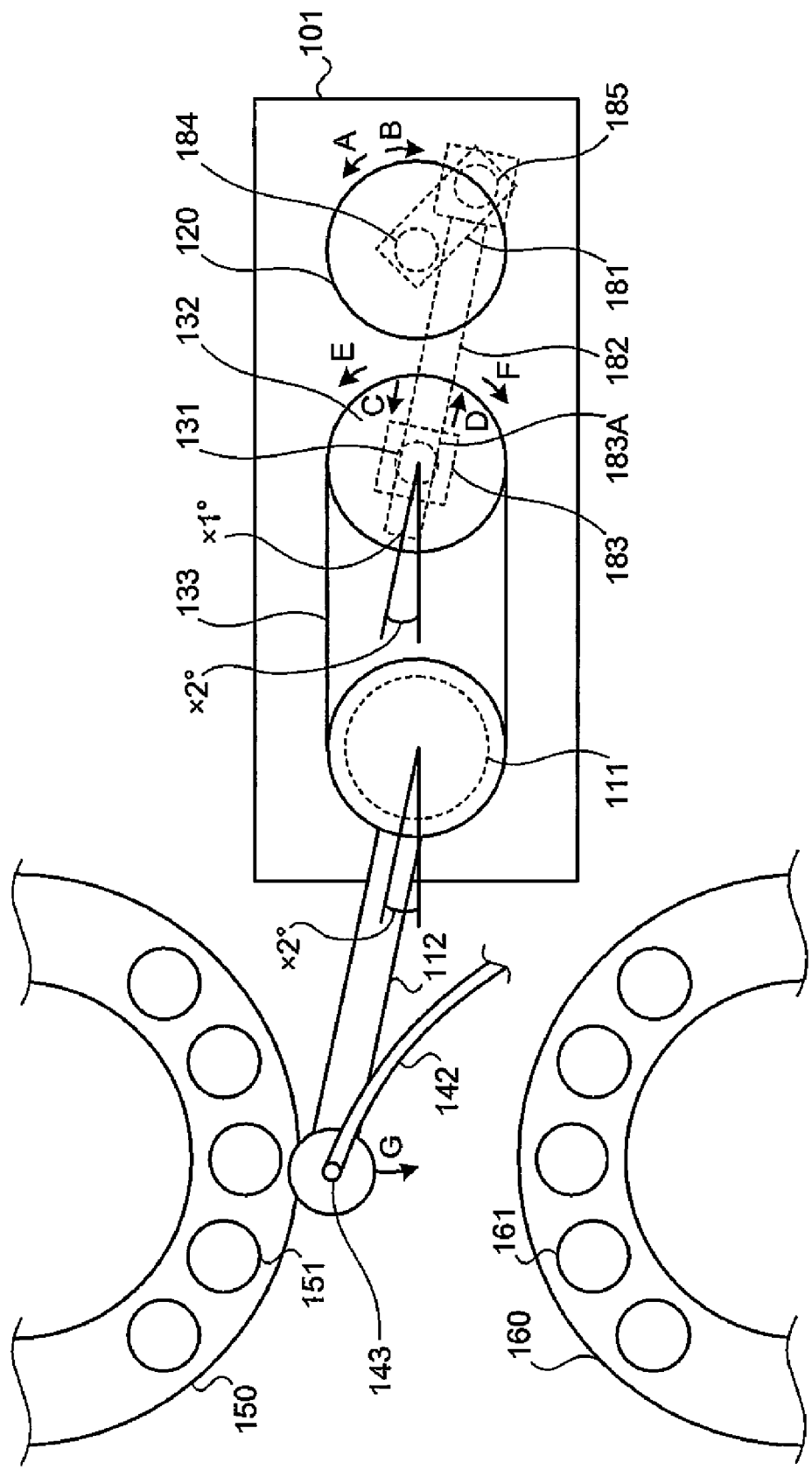
FIG. 5 is a plan view of the dispensing apparatus when the dispensing nozzle held at the distal end of the dispensing arm rotates toward the predetermined discharge position from a state of being positioned at the predetermined drawing position.

An operation of the dispensing apparatus 100 when the dispensing arm 110 starts rotating is explained with reference to FIGS. 5 and 6. FIG. 5 is a plan view of the dispensing apparatus 100 when the dispensing nozzle 143 held at the distal end of the dispensing arm 110 rotates toward the predetermined discharge position from a state of being positioned at the predetermined drawing position.

As shown in FIG. 5, the crank lever 181 that rotates through a driving force of the driving motor 120 is rotated approximately 45° in the direction A through a driving force of the driving motor 120 under the control of the non-depicted computer from a state where the crank pin 185 that couples the crank lever 181 with the crank rod 182 is positioned at a position corresponding to the predetermined drawing position.

When the crank pin 185 is rotated approximately 45° from the position corresponding to the predetermined drawing position, the crank rod 182 coupled with the crank pin 185 and the crank rod slider 183 slides through the through hole 183A formed in the crank rod slider 183 along the direction D, the incline of the crank rod 182 already inclined at X1° is eliminated, and the crank rod 182 inclines X2°.

When the incline of the crank rod 182 is eliminated, the crank rod slider 183, the drive shaft 131, and the driving pulley 132 are further rotated along the direction E. When the driving pulley 132 is further rotated along the direction E, the dispensing arm 110 is further rotated along a direction G. When the dispensing arm 110 is further rotated along the direction G, the incline of the dispensing arm 110 already inclined at X1° is eliminated, and the dispensing arm 110 inclines X2°.

Figure 6:
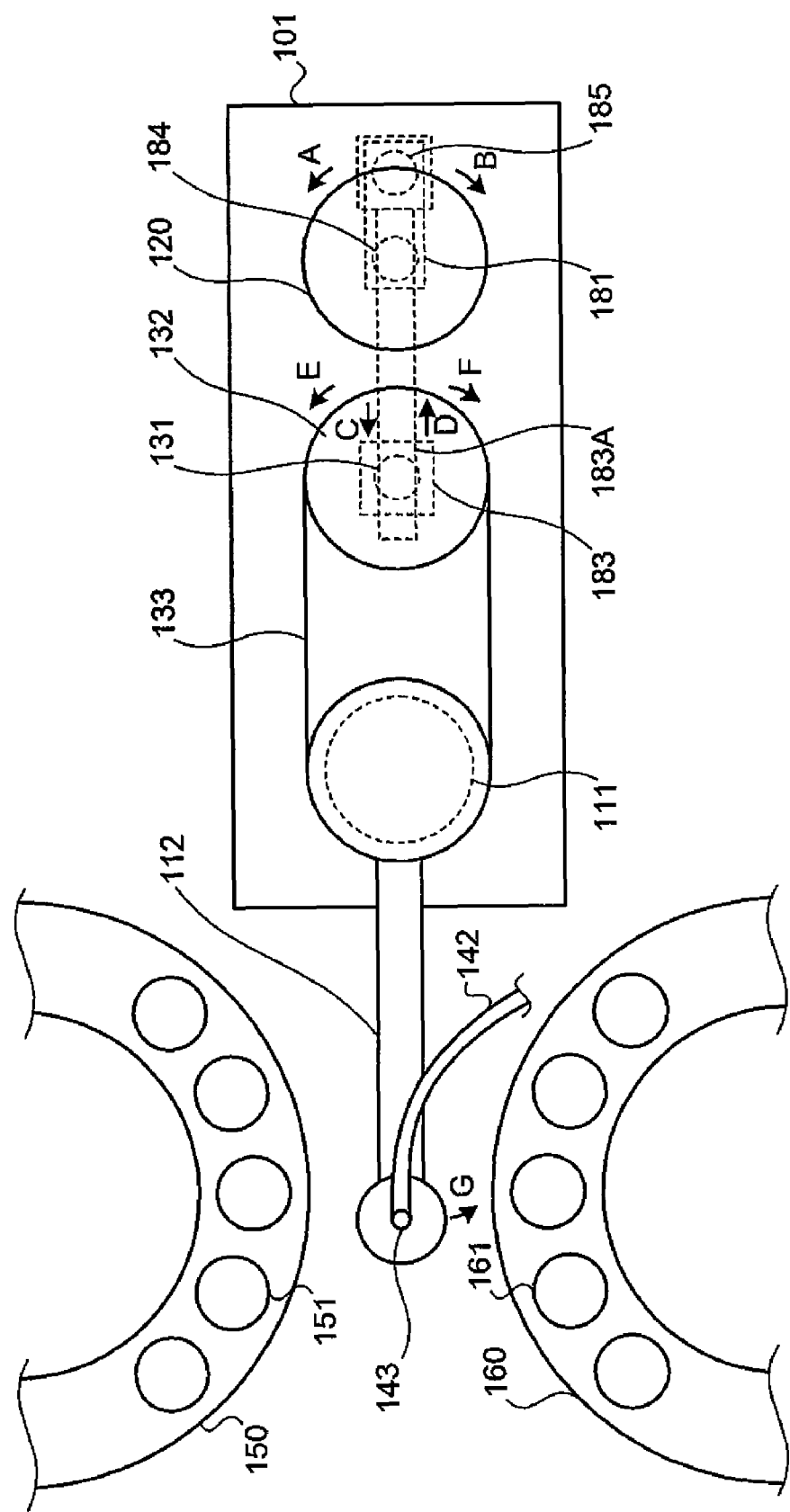
FIG. 6 is a plan view of the dispensing apparatus when the dispensing nozzle held at the distal end of the dispensing arm further rotates toward the predetermined discharge position.

FIG. 6 is a plan view of the dispensing apparatus 100 when the dispensing nozzle 143 held at the distal end of the dispensing arm 110 further rotates toward the predetermined discharge position from the state of the dispensing apparatus depicted in FIG. 5.

As shown in FIG. 6, the crank lever 181 that rotates through a driving force of the driving motor 120 is further rotated approximately 45° (i.e., approximately 90° along the direction A from a state where the crank pin 185 is positioned at the position corresponding to the predetermined drawing position) along the direction A through a driving force of the driving motor 120 under the control of the non-depicted computer from a state where the crank pin 185 that couples the crank lever 181 with the crank rod 182 is rotated approximately 45° along the direction A (state depicted in FIG. 5) from a state of positioning at the position corresponding to the predetermined drawing position.

When the crank pin 185 is further rotated approximately 45°, the crank rod 182 coupled with the crank pin 185 and the crank rod slider 183 further slides through the through hole 183A formed in the crank rod slider 183 along the direction D, the incline is eliminated in the crank rod 182 already inclined at X2°, and the crank rod 182 enters a state of incline of 0° (i.e., a state of no incline).

The crank rod slider 183, the drive shaft 131, and the driving pulley 132 are further rotated along the direction E due to elimination of the incline in the crank rod 182. Since the driving pulley 132 is further rotated along the direction E, the dispensing arm 110 is further rotated along the direction G by the driving belt 133.

Since the dispensing arm 110 is further rotated along the direction G, the incline is eliminated in the dispensing arm 110 already inclined at X2°, and the dispensing arm 110 enters a state of incline of 0° (i.e., a state of no incline).

(Operation of Dispensing Apparatus 100 when Dispensing Arm 110 Stops Rotating)

Figure 7:
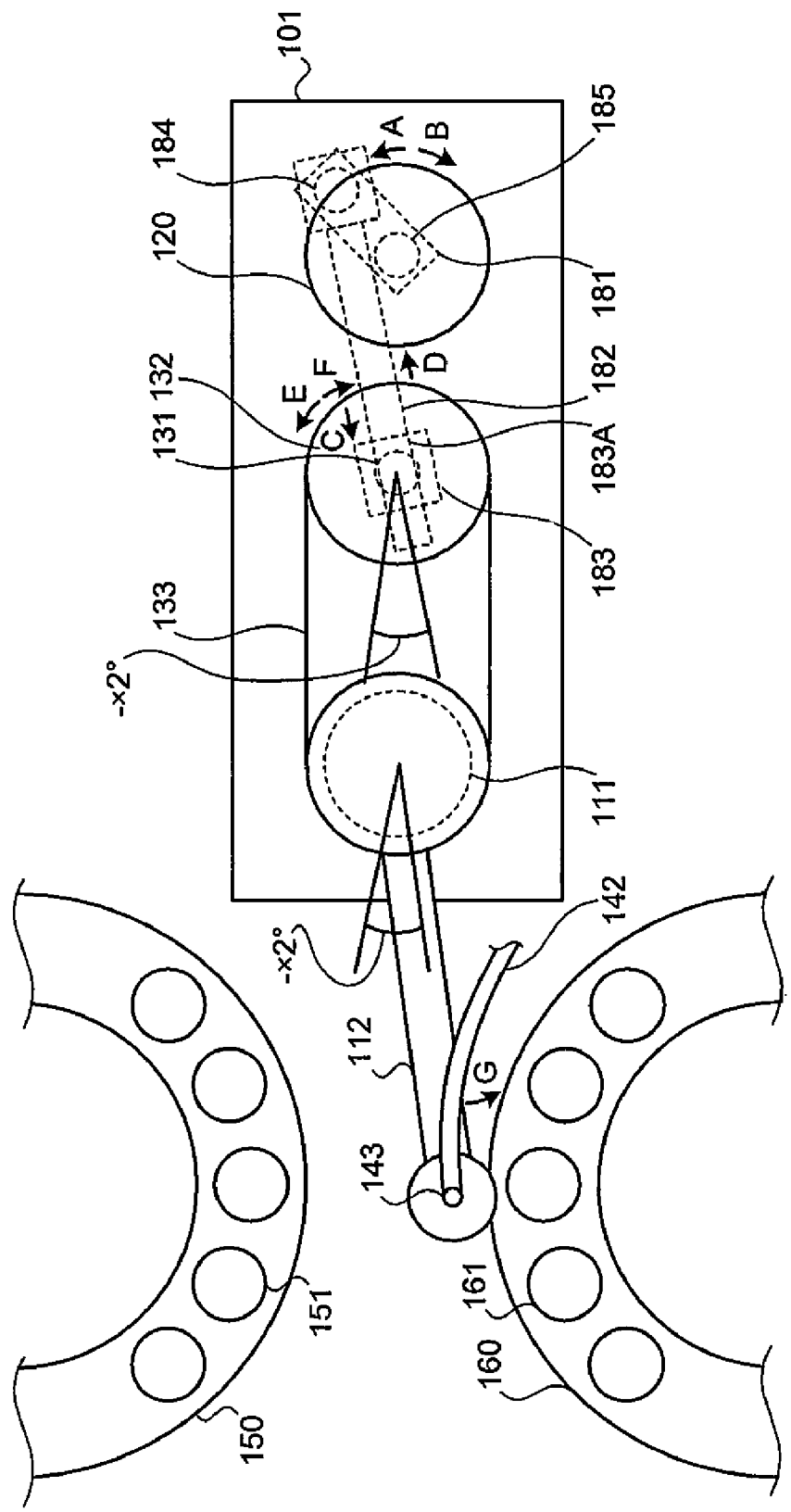
FIG. 7 is a plan view of the dispensing apparatus when the dispensing nozzle held at the distal end of the dispensing arm further rotates toward the predetermined discharge position.

An operation of the dispensing apparatus 100 when the dispensing arm 110 stops rotating is explained with reference to FIGS. 7 and 8. FIG. 7 is a plan view of the dispensing apparatus 100 when the dispensing nozzle 143 held at the distal end of the dispensing arm 110 further rotates toward the predetermined discharge position from the state of the dispensing apparatus 100 explained with reference to FIG. 6.

As shown in FIG. 7, the crank lever 181 is further rotated approximately 45° (i.e., approximately 135° toward the direction A from a state where the crank pin 185 is positioned at a position corresponding to the predetermined drawing position) along the direction A through a driving force of the driving motor 120 under the control of the non-depicted computer from a state where the crank pin 185 that couples the crank lever 181 with the crank rod 182 is rotated approximately 90° toward the direction A (state depicted in FIG. 6) from a state where the crank pin 185 is positioned at the position corresponding to the predetermined drawing position.

Since the crank pin 185 is further rotated approximately 45°, the crank rod 182, which is coupled with the crank pin 185 and the crank rod slider 183, slides through the through hole 183A formed in the crank rod slider 183 toward the direction C, and the crank rod 182 inclines −X2°.

Since the crank rod 182 inclines −X2°, the crank rod slider 183, the drive shaft 131, and the driving pulley 132 are further rotated X2° in the direction E. Since the driving pulley 132 is further rotated X2° along the direction E, the dispensing arm 110 is further rotated X2° in the direction G by the driving belt 133. Since the dispensing arm 110 is further rotated X2° in the direction G, the dispensing arm 110 inclines −X2°, and the dispensing arm 110 enters a state of incline of −X2°.

Figure 8:
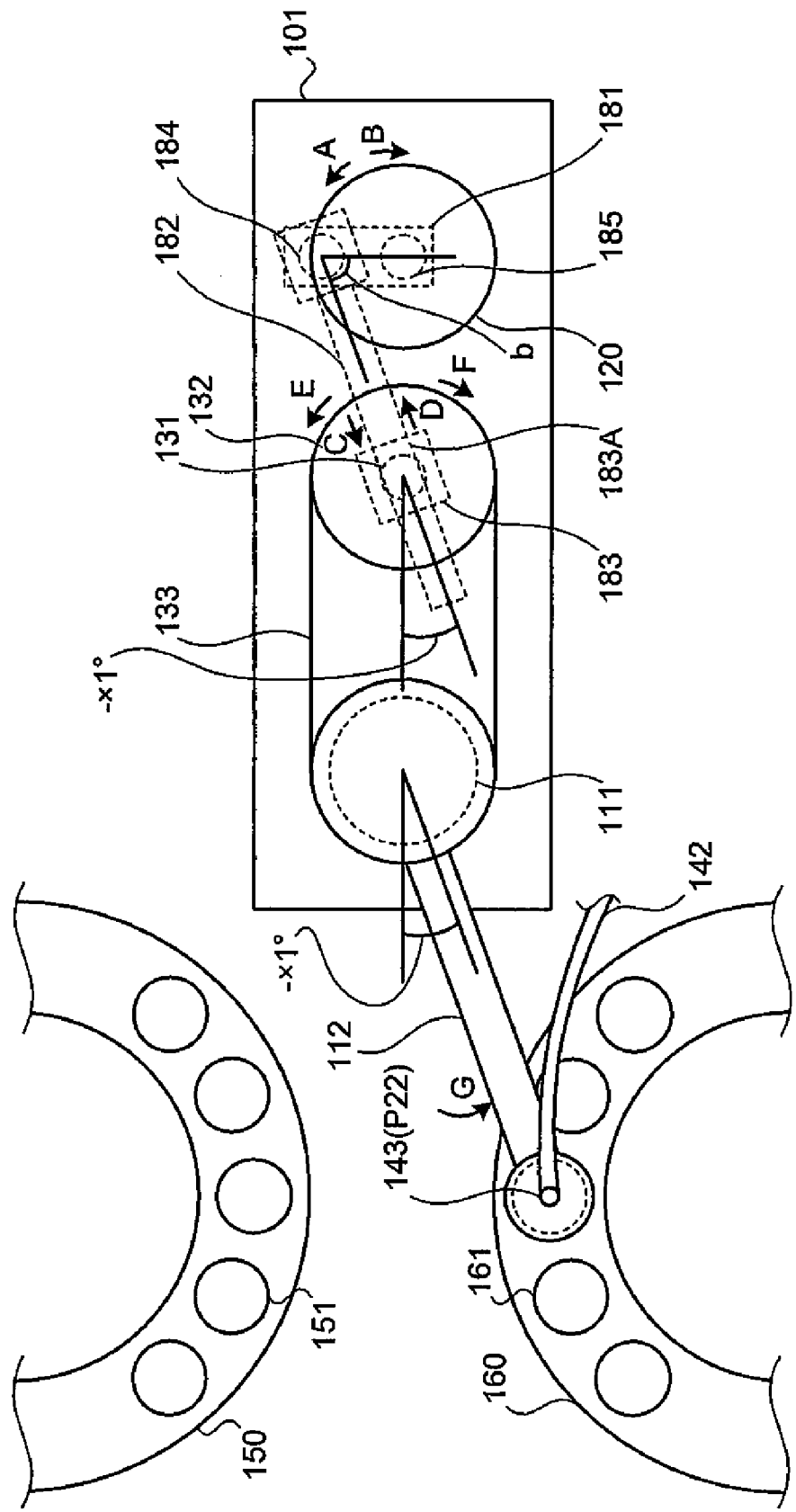
FIG. 8 is a plan view of the dispensing apparatus when the dispensing nozzle held at the distal end of the dispensing arm is positioned at the predetermined discharge position.

FIG. 8 is a plan view of the dispensing apparatus 100 when the dispensing arm 110 further rotates toward the predetermined discharge position from the state of the dispensing apparatus 100 explained with reference to FIG. 7 and the dispensing nozzle 143 held at the distal end of the dispensing arm 110 is positioned at the predetermined discharge position.

As shown in FIG. 8, the crank lever 181 is further rotated approximately 45° (i.e., approximately 180° toward the direction A from a state where the crank pin 185 is positioned at a position corresponding to the predetermined drawing position) in the direction A through a driving force of the driving motor 120 under the control of the non-depicted computer from a state where the crank pin 185 that couples the crank lever 181 with the crank rod 182 is rotated approximately 135° toward the direction A from a situation where the crank pin 135 is positioned at the position corresponding to the predetermined drawing position, and rotating of the crank pin 185 is stopped under the control of the non-depicted computer in a state where it is positioned at a position corresponding to the predetermined discharge position.

Since the crank pin 185 is further rotated approximately 45° to be positioned at the position corresponding to the predetermined discharge position, the crank rod 182 coupled with the crank pin 185 and the crank rod slider 183 further slides through the through hole 183A formed in the crank rod slider 183 along the direction C, the crank rod 182 already inclined at −X2° is further inclined, and the crank rod 182 enters a state of incline of −X1°. At this time, an intersecting angle (an angle b) of the crank lever 181 and the crank rod 182 must fall within 90°, and 90° being the most desirable.

Since the crank rod 182 is further inclined, the crank rod slider 183, the drive shaft 131, and the driving pulley 132 are further rotated along the direction E. Since the driving pulley 132 is further rotated along the direction E, the dispensing arm 110 is further rotated along the direction G by the driving belt 133.

Since the dispensing arm 110 is further rotated toward the direction G, the dispensing arm 110 already inclined at −X2° further inclines, the dispensing arm 110 enters a state of incline of −X1°, and the dispensing nozzle 143 held at the distal end of the dispending arm 110 is positioned at the predetermined discharge position (P22).

Moving the dispensing nozzle 143 downward together with the dispensing arm 110 from the state where the dispensing nozzle 143 is positioned, in this manner, at the predetermined discharge position (P22) enables insertion of the distal end of the dispensing nozzle 143 into the specimen container 161. When the distal end of the dispensing nozzle 143 is inserted in the specimen container 161, generation of a pressure (a positive pressure) by the syringe pump unit 141 enables discharge of the reagent 152 from the distal end of the dispensing nozzle 143 into the specimen container 161.

(Change in Rotational Speed of Dispensing Arm 110 and Change in Inertial Load of Dispensing Arm 110)

In the operations of the dispensing apparatus 100 explained with reference to FIGS. 4 to 8, the crank rod 182, which rotates while changing an incline angle thereof with rotation of the crank lever 181, rotates while gradually increasing a variation in incline angle so that the dispensing arm 110 starts rotating while gradually increasing a variation in rotational speed from the predetermined drawing position (P21). The crank rod 182 rotates while gradually reducing a variation in incline angle so that the dispensing arm 110 stops rotating while gradually reducing a variation in rotational speed at the predetermined discharge position (P22).

Based on such operations, the dispensing arm 110 starts rotating from a state of being stopped at the predetermined drawing position (P21) (a state where the rotational speed is zero), gradually accelerates without a sudden change in rotational speed as depicted in later-explained FIG. 9, and rotates toward the predetermined discharge position (P22) without a sudden change in inertial load as depicted in later-explained FIG. 10. The rotational speed of the dispensing arm 110 becomes maximum at the time when the dispending arm 110 reaches an intermediate position between the predetermined drawing position (P21) and the predetermined discharge position (P22).

The dispensing arm 110 gradually decelerates from the intermediate position between the predetermined drawing position (P21) and the predetermined discharge position (P22) without a sudden change in rotational speed as depicted in later-explained FIG. 9, and rotates toward the predetermined discharge position (P22) without a sudden change in inertial load as depicted in later-explained FIG. 10. The dispensing arm 110 stops rotating at the same time the rotation of the dispensing arm 110 reaches the predetermined discharge position (P22).

Figure 9:
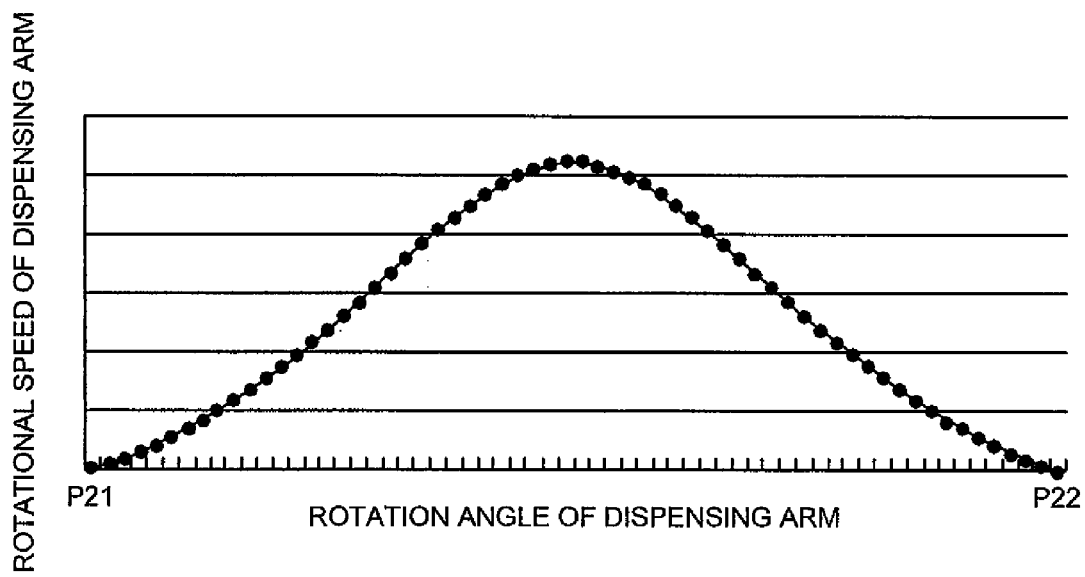
FIG. 9 is a graph of an example of a change in rotational speed of the dispensing arm in the dispensing apparatus according to the first embodiment of the present invention.

FIG. 9 is a graph of an example of a change in rotational speed of the dispensing arm 110 in the dispensing apparatus 100 according to the first embodiment of the present invention. In FIG. 9, an ordinate represents a rotational speed of the dispensing arm 110, and an abscissa represents a rotation angle of the dispensing arm 110. As shown in FIG. 9, the rotational speed of the dispensing arm 110 is gradually increased without a sudden change while the rotation angle of the dispensing arm 110 falls within the range from the predetermined drawing position to the intermediate position between the predetermined drawing position (P21) and the predetermined discharge position (P22).

The rotational speed of the dispensing arm 110 becomes maximum at the rotation angle of the dispensing arm 110 when positioned at an intermediate position between the predetermined drawing position (P21) and the predetermined discharge position (P22). The rotational speed of the dispensing arm 110 is gradually reduced without a sudden change while the rotation angle of the dispensing arm 110 falls within the range from the intermediate position between the predetermined drawing position (P21) and the predetermined discharge position (P22) to the predetermined discharge position (P22).

In this manner, as shown in FIG. 9, the rotational speed of the dispensing arm 110 gently varies without a sudden change from the start of rotation of the dispensing arm 110 at the predetermined drawing position (P21) to the end of rotation of the same at the predetermined discharge position (P22).

Figure 10:
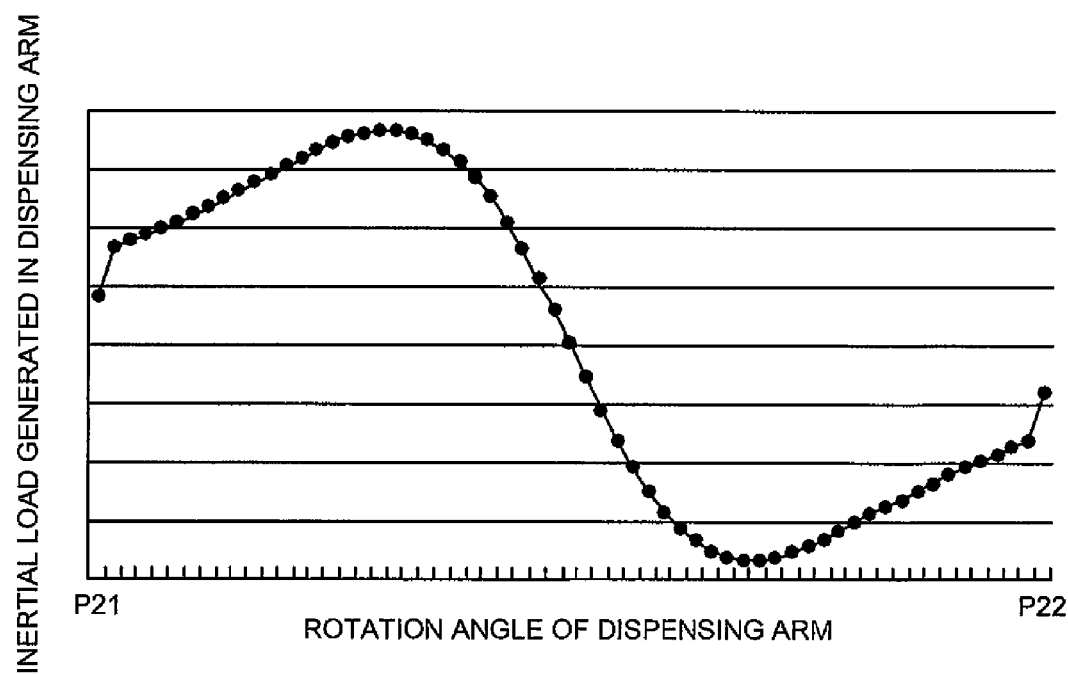
FIG. 10 is a graph of an example of a change in inertial load generated in the dispensing arm of the dispensing apparatus according to the first embodiment of the present invention.

FIG. 10 is a graph of an example of a change in inertial load generated in the dispensing arm 110 of the dispensing apparatus 100 according to the first embodiment of the present invention. In FIG. 10, an ordinate represents an inertial load generated in the dispensing arm 110, and an abscissa represents a rotation angle of the dispensing arm 110. As shown in FIG. 10, an inertial load generated in the dispensing arm 110 gently varies without a sudden change from the start of rotation of the dispensing arm 110 at the predetermined drawing position (P21) until the end of rotation at the predetermined discharge position (P22).

In this manner, according to the dispensing apparatus 100 according to the first embodiment, a driving force of the driving motor 120 is transmitted to the dispensing arm 110 through the transmission/buffering unit 180 including the crank shaft 184 that rotates through a driving force of the driving motor 120 and the crank rod 182 that is coupled with the crank shaft 184 and rotates based on rotating of the crank shaft 184, thereby rotating the dispensing arm 110. As a result, even if a sudden change occurs in the driving force of the driving motor 120, the dispensing arm 110 can be rotated without generating vibrations or impact shocks associated with a sudden change in the rotational speed or a sudden change in inertial load with respect to the dispensing arm 110.

When the dispensing arm 110 is rotated without producing vibrations or impact shocks with respect to the dispensing arm 110, the dispensing nozzle 143 can be carried to the predetermined discharge position without dispersion of the reagent 152 drawn from the reagent container 151 by the dispensing nozzle 143 held at the distal end of the dispensing arm 110, and the reagent 152 can be discharged into the specimen container 161. As a result, precision when dispensing the reagent 152 into the specimen container 161 by the dispensing apparatus 100 can be improved.

In the dispensing apparatus 100 according to the first embodiment, operation may be such that the crank pin 185 that couples the crank lever 181 with the crank rod 182 is rotated from the position corresponding to the predetermined discharge position to the position corresponding to the predetermined drawing position through a driving force of the motor 120, i.e., the inverse of the operation explained with reference to FIGS. 6 to 10. In this case as well, the dispensing arm 110 can be rotated without vibration or impact shock.

(Another Structural Example of Dispensing Apparatus 100)

Figure 11:
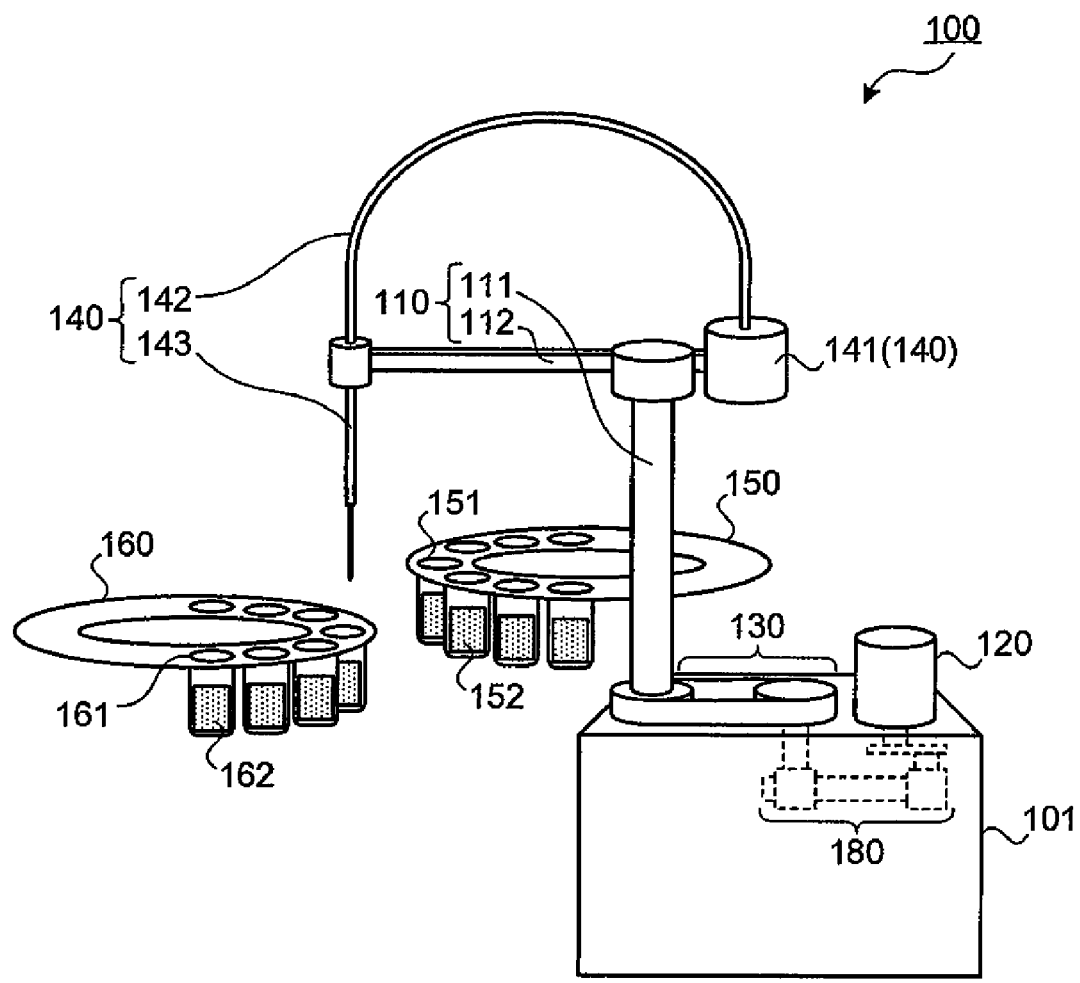
FIG. 11 is a perspective view of the dispensing apparatus according to the first embodiment of the present invention.

Another structural example of the dispensing apparatus 100 is explained with reference to FIG. 11. FIG. 11 is a perspective view of the dispensing apparatus 100 according to the first embodiment of the present invention. As shown in FIG. 11, the dispensing apparatus 100 is different from the dispensing apparatus 100 explained with reference to FIG. 1 in that the syringe pump unit 141 included in the drawing/discharging unit 140 is provided above the dispensing arm shaft 111 included in the dispensing arm 110 with respect to the dispensing apparatus 100 explained with reference to FIG. 1.

This apparatus is also different from the dispensing apparatus 100 explained with reference to FIG. 1 in that a length of the syringe pump pipe 142 that transmits pressure from the syringe pump unit 141 to the dispensing nozzle 143 is reduced since the syringe pump unit 141 is provided above the dispensing arm shaft 111.

By disposing the syringe pump unit 141 above the dispensing arm shaft 111, installation space for the dispensing apparatus 100 depicted in FIG. 11 can be reduced and the size of the dispensing apparatus 100 can also be reduced. The length of the syringe pump pipe 142 can be shortened, and a metal material can be used for a part of or for the entire the syringe pump pipe 142 in some cases. As a result, a reduction in pressure transmitted to the dispensing nozzle 143 or an increase in transmission time of the pressure transmitted resulting from vibrations or expansion of the syringe pump pipe 142 can be avoided, thereby improving dispensing precision (an accuracy of a drawing amount of the reagent 152 or an accuracy of a discharge amount of the reagent 152) of the dispensing apparatus 100 and reducing dispensing time.

Even if a heavy load (the syringe pump unit 141 having a weight of, for example, 400 grams) is mounted on the dispensing arm 110 and the weight of the dispensing arm 110 is increased, since a driving torque of the driving motor 120 is increased by the transmission/buffering unit 180, the dispensing arm 110 can be rotated by using a small driving force without affecting variations in rotational speed or in inertial load of the dispensing arm 110. Therefore, even if the driving motor 120 is small or has low power consumption, the dispensing arm 110 having an increased weight can be rotated.

Second Embodiment

Structure of Dispensing Apparatus 1200

Figure 12:
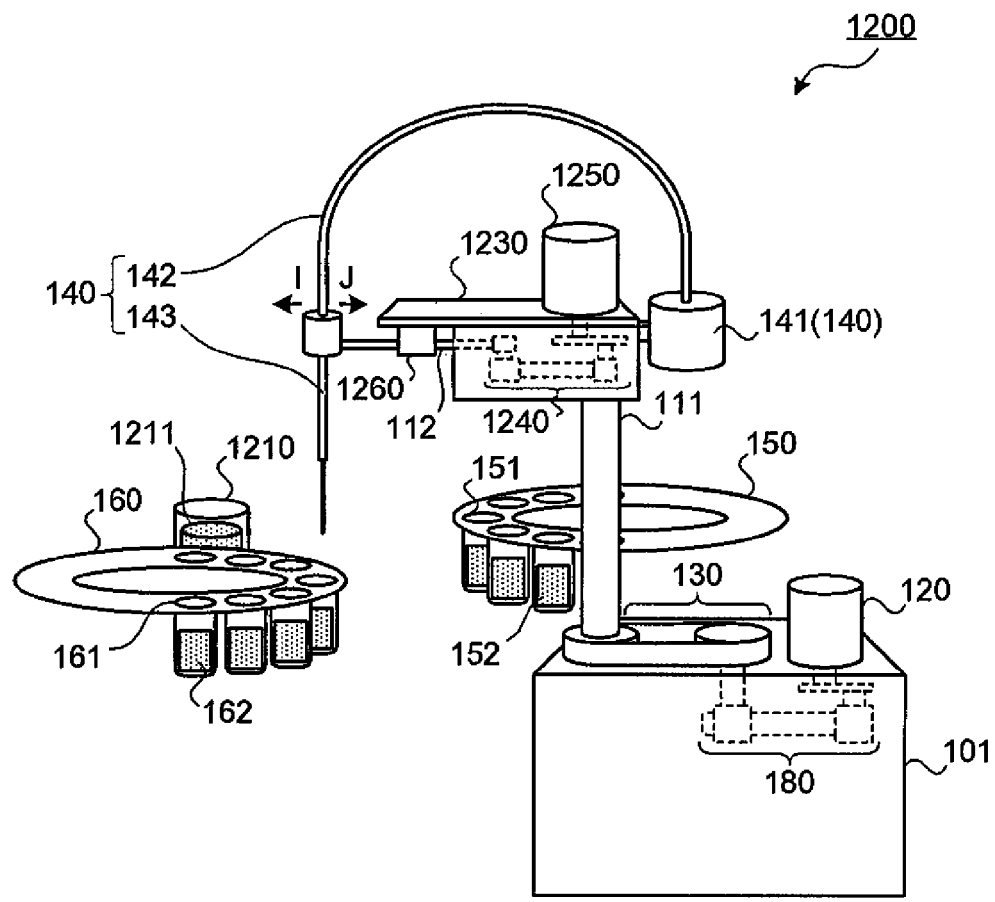
FIG. 12 is a perspective view of a dispensing apparatus according to a second embodiment of the present invention.

A structure of a dispensing apparatus 1200 according to the second embodiment is explained with reference to FIG. 12. FIG. 12 is a perspective view of the dispensing apparatus 1200 according to the second embodiment of the present invention. As shown in FIG. 12, the dispensing apparatus 1200 discharges a reagent 152 drawn from a reagent container 151 arranged in a reagent table 150 into a specimen container 161 that is arranged in a specimen table 160 and holds a specimen 162 therein.

The dispensing apparatus 1200 can clean a dispensing nozzle 143 held at a distal end of an arm 112 utilizing a cleaning device 1210 by extending the arm 112 after discharging the reagent 152 into the specimen container 161. The dispensing apparatus 1200 includes a second case 1230 for extending and retracting the arm 112, a second transmission/buffering unit 1240, a second driving motor 1250, and an arm slider 1260 in addition to structures identical to those of the dispensing apparatus 100 explained in the first embodiment. Like reference numerals denote like structures explained in the first embodiment and explanation thereof is omitted.

The second case 1230 is of a rectangular shape, where the second driving motor 1250 mounted to an upper portion thereof and the second transmission/buffering unit 1240 is enclosed therein. The second case 1230 is pivotally supported by an arm shaft 111, and rotates together with a dispensing arm 110 and the arm 112 through a driving force of the driving motor 120. An upper surface of the second case 1230 protrudes in a direction toward the arm 112.

The second transmission/buffering unit 1240 extends and retracts the arm 112 through a driving force of the second driving motor 1250. The second transmission/buffering unit 1240 absorbs a sudden change in rotational speed that occurs with the second driving motor 1250 when, for example, extension/retraction of the arm 112 starts or extension/retraction of the arm 112 stops, and alleviates a change in extension/retraction speed of the arm 112 that extends and retracts through a driving force of the second driving motor 1250.

Figure 13:
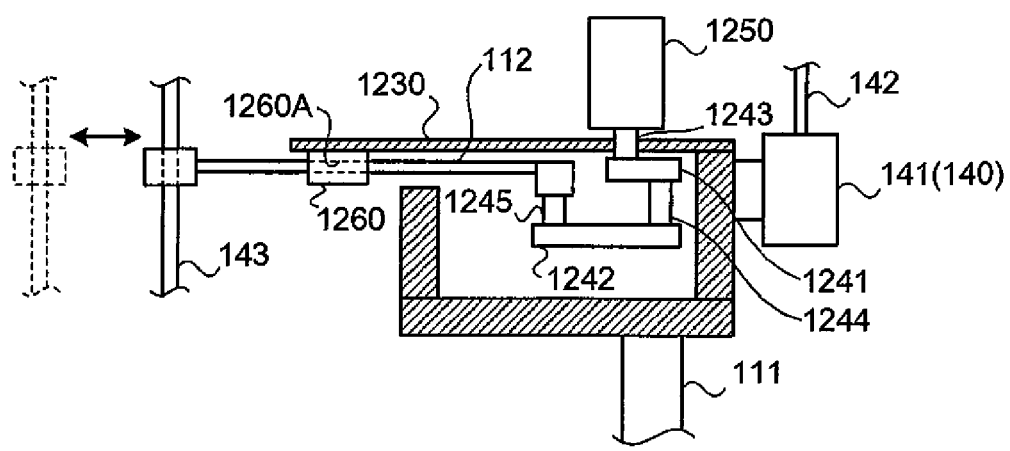
FIG. 13 is a side view of a second transmission/buffering unit.

The second driving motor 1250 is a motor (an alternating-current motor or a direct-current motor) that is driven under the control of a non-depicted computer to extend and retract the arm 112 through the second transmission/buffering unit 1240. The arm slider 1260 is formed near a distal end of a rear side of the upper surface of the second case 1230 protruding in the direction of the arm 112. A later-explained through hole 1260A depicted in FIG. 13 is formed in the arm slider 1260, and the arm 112 is inserted and fitted in this hole so that the arm 112 can be slidable in an extending direction (a direction I) and a retracting direction (a direction J).

(Structure of Second Transmission/Buffering Unit 1240)

Figure 14:
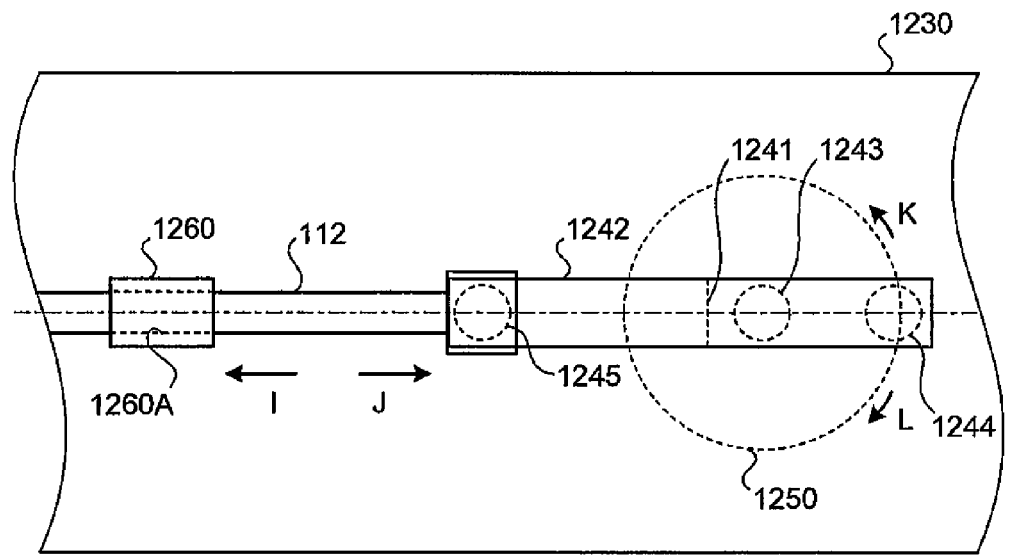
FIG. 14 is a plan view of the second transmission/buffering unit.

Details of a structure of the second transmission/buffering unit 1240 are explained with reference to FIGS. 13 and 14. FIG. 13 is a side view of the second transmission/buffering unit 1240. FIG. 14 is a plan view of the second transmission/buffering unit 1240. As shown in FIGS. 13 and 14, the second transmission/buffering unit 1240 includes a second crank lever 1241, a second crank rod 1242, a second crank shaft 1243, a second crank pin 1244, and a piston pin 1245.

The second crank lever 1241 converts a rotating motion of the second crank shaft 1243 generated through a driving force of the second driving motor 1250 into an extending/retracting motion of the arm 112, is coupled with the second crank shaft 1243, and rotates together with the second crank shaft 1243. The second crank rod 1242 is coupled with the second crank lever 1241 through the second crank pin 1244 arranged at a distal end of the second crank lever 1241 to allow a rotating motion of the second crank rod 1242.

The second crank lever 1241 rotates together with the second crank shaft 1243 in a retracting direction (a direction K) of the arm 112 and an extending direction (a direction L) of the arm 112 through a driving force of the second driving motor 1250, thereby rotating the second crank rod 1242 coupled thereto by the second crank pin 1244.

The second crank rod 1242 has a bar-like shape and couples the second crank lever 1241 with the arm 112 so that the arm 112 can extend and retract with rotation of the second crank lever 1241. The second crank rod 1242 has one end coupled with the second crank lever 1241 by the second crank pin 1244 and the other end coupled with the arm 112 by the piston pin 1245.

The second crank shaft 1243 rotates interlocked with driving of the second driving motor 1250. The second crank shaft 1243 is coupled with the second crank lever 1241 and rotates the second crank lever 1241. The second crank pin 1244 couples the second crank lever 1241 with the second crank rod 1242 to allow a rotating motion. The piston pin 1245 couples the arm 112 with the second crank rod 1242.

(State of Second Transmitting/Buffering Unit 1240 when Dispensing Nozzle 143 is Positioned at Predetermined Discharge Position)

Figure 15:
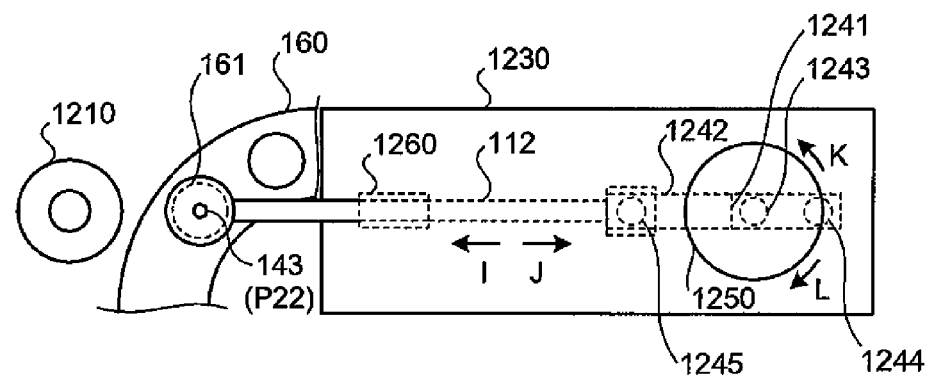
FIG. 15 is a plan view of the dispensing apparatus when the dispensing nozzle held at a distal end of the arm is positioned at the predetermined discharge position.

An operation of the thus configured second transmission/buffering unit 1240 is explained with reference to FIGS. 15 to 17. A state of the second transmission/buffering unit 1240 when the dispensing nozzle 143 is positioned at a predetermined discharge position is first explained with reference to FIG. 15. FIG. 15 is a plan view of the dispensing apparatus 100 when the dispensing nozzle 143 held at a distal end of the arm 112 is positioned at the predetermined discharge position.

As shown in FIG. 15, operation of the second driving motor 1250 is stopped under the control of a non-depicted computer and rotation of the second crank lever 1241 that rotates through a driving force of the second driving motor 1250 is stopped in a state where the second crank pin 1244, which couples the second crank lever 1241 with the second crank rod 1242 to allow a rotating motion, is positioned at a position corresponding to the predetermined discharge position.

When the second crank pin 1244 that couples the second crank lever 1241 with the second crank rod 1242 is positioned at a position corresponding to a predetermined drawing position, the arm 112 coupled with the second crank lever 1241 through the second crank rod 1242 enters the most retracted state. As a result, the dispensing nozzle 143 held at the distal end of the arm 112 enters a state where it is positioned at the predetermined discharge position (P22).

The dispensing apparatus 1200 moves the arm 112 downward together with the dispensing arm shaft 111 from such a state, discharges the reagent 152 into the specimen container 161 from the dispensing nozzle 143 held at the distal end of the arm 112, then moves the arm 112 upward together with the dispensing arm shaft 111, and further extends the arm 112, thereby placing the dispensing nozzle 143 held at the distal end of the arm 112 at a predetermined cleaning position to clean the dispensing nozzle 143 by the cleaning device 1210.

(Operation of Second Transmission/Buffering Unit 1240 when Arm 112 Extends)

An operation of the second transmission/buffering unit 1240 when the arm 112 extends is explained with reference to FIG. 16. FIG. 16 is a plan view of the second transmission/buffering unit 1240 when the dispensing nozzle 143 held at the distal end of the arm 112 extends toward the predetermined cleaning position from a state where the dispensing nozzle 143 is positioned at the predetermined discharge position.

Figure 16:
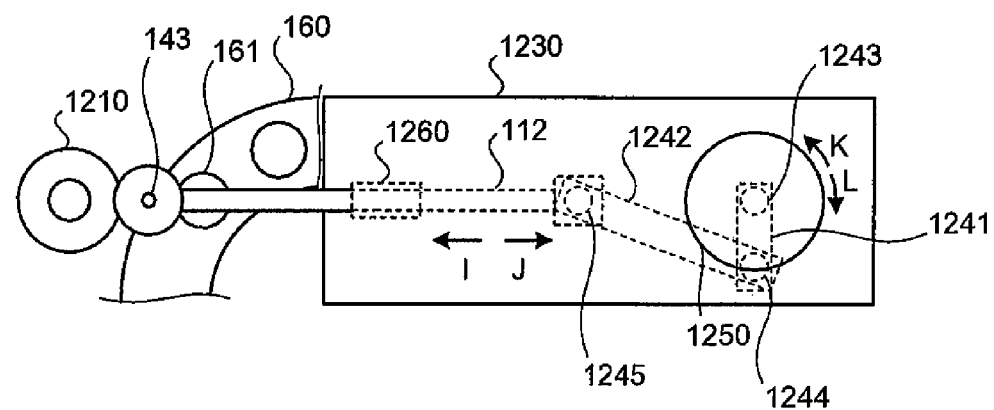
FIG. 16 is a plan view of the second transmission/buffering unit when the dispensing nozzle held at the distal end of the arm extends toward a predetermined cleaning position from a state where the dispensing nozzle is positioned at the predetermined discharge position.

As shown in FIG. 16, the second crank lever 1241 that rotates through a driving force of the second driving motor 1250 is rotated approximately 90° in the direction L through a driving force of the second driving motor 1250 under the control of the non-depicted computer from a state where the second crank pin 1244 that couples the second crank lever 1241 with the second crank rod 1242 is positioned at the position corresponding to the predetermined discharge position.

When the second crank pin 1244 is rotated approximately 90° from the position corresponding to the predetermined discharge position, the arm 112 coupled with the second crank lever 1241 through the second crank rod 1242 slides and extends through the through hole 1260A formed in the arm slider 1260 along the direction I.

(State of Second Transmission/Buffering Unit 1240 when Dispensing Nozzle 143 is Positioned at Predetermined Cleaning Position)

A state of the second transmission/buffering unit 1240 when the dispensing nozzle 143 is positioned at the predetermined cleaning position is explained with reference to FIG. 17. FIG. 17 is a plan view of the second transmission/buffering unit 1240 when the arm 112 further extends toward the predetermined cleaning position from the state of the second transmission/buffering unit 1240 explained with reference to FIG. 16 and the dispensing nozzle 143 held at the distal end of the arm 112 is positioned at the predetermined cleaning position.

Figure 17:
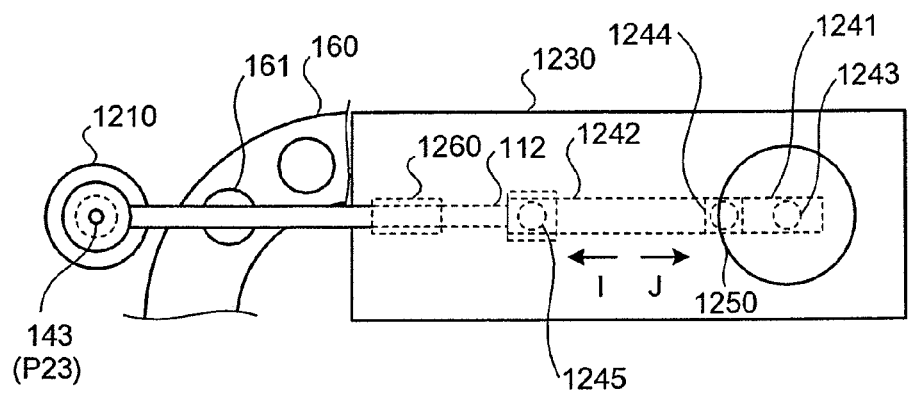
FIG. 17 is a plan view of the second transmission/buffering unit when the dispensing nozzle held at the distal end of the arm is positioned at the predetermined cleaning position.
Figure 18:
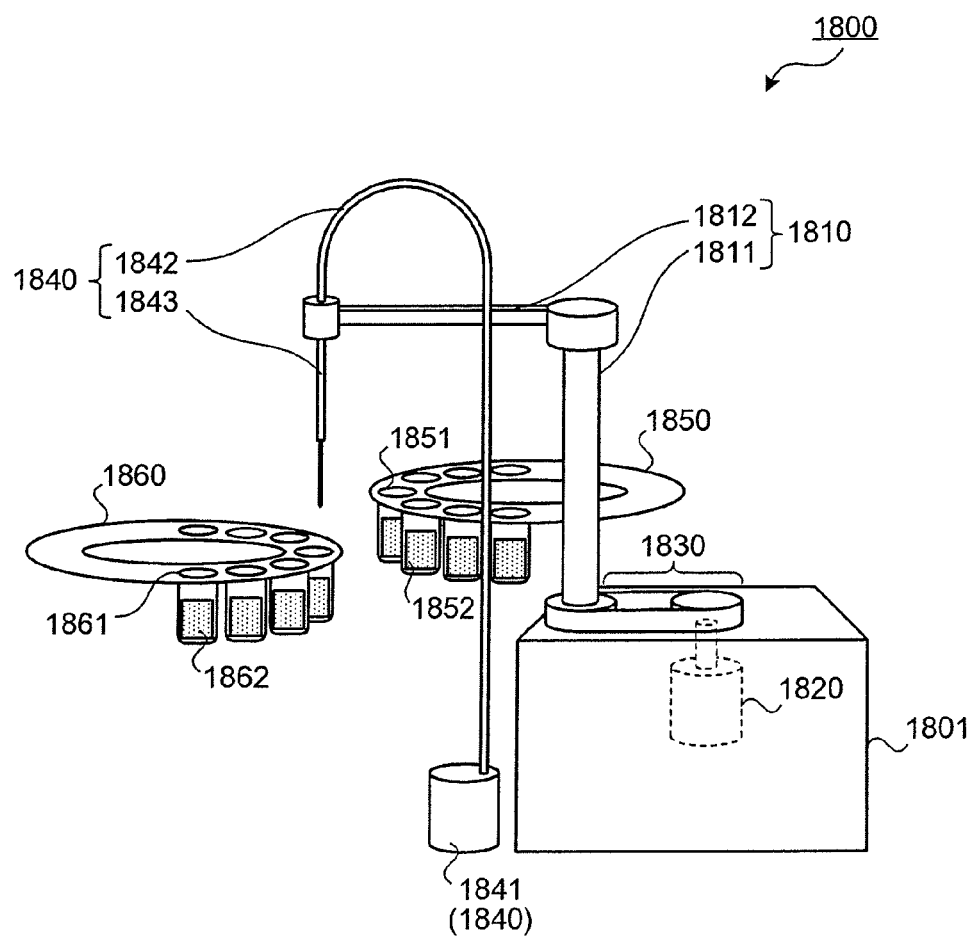
FIG. 18 is a perspective view of a conventional dispensing apparatus utilizing the conventional technology.

As shown in FIG. 17, the second crank lever 1241 that rotates through a driving force of the second driving motor 1250 is further rotated approximately 90° along the direction L through a driving force of the second driving motor 1250 under the control of the non-depicted computer from the state where the second crank pin 1244 that couples the second crank lever 1241 with the second crank rod 1242 is rotated approximately 90° along the direction L (the state depicted in FIG. 16) from the state of being positioned at a position corresponding to the predetermined discharge position. FIG. 17 depicts a state where operation of the second driving motor 1250 is stopped under the control of the non-depicted computer and rotation of the second crank pin 1244 is stopped in a state where the second crank pin 1244 is positioned at the predetermined cleaning position.

Since the second crank pin 1244 is further rotated approximately 90° along the direction L, the arm 112 further slides and extends through the through hole 1260A formed in the arm slider 1260 along the direction I.

Since the arm 112 further slides and extends through the through hole 1260A formed in the arm slider 1260 along the direction I, the arm 112 enters the most extended state. As a result, the dispensing nozzle 143 held at the distal end of the arm 112 enters a state where it is positioned at the predetermined cleaning position (P23).

The dispensing apparatus 1200 moves the arm 112 downward together with the dispensing arm shaft 111 from such a state to insert the dispensing nozzle 143 held at the distal end of the arm 112 into the cleaning device 1210, thereby cleaning the dispensing nozzle 143 by using the cleaning device 1210.

(Change in Extending Speed of Arm 112 and Change in Inertial Load of Dispensing Arm 110)

On the other hand, the arm 112, which extends through the second transmission/buffering unit 1240 through a driving force of the second driving motor 1250, starts extending from the state where it is stopped at the predetermined discharge position (P22) (a state where an extending speed is zero), gradually accelerates without a sudden change in extending speed, and extends toward the predetermined cleaning position (P23) without a sudden change in inertial load. The extending speed becomes maximum at the time when the arm 112 reaches an intermediate position between the predetermined discharge position (P22) and the predetermined cleaning position (P23).

The arm 112 gradually extends toward the predetermined cleaning position (P23) without a sudden change in inertial load while gradually decelerating from the intermediate position between the predetermined discharge position (P22) and the predetermined cleaning position (P23) without a sudden change in extending speed. Extension of the arm 112 stops at the time when extension of the arm 112 reaches the predetermined cleaning position (P23).

In this manner, according to the dispensing apparatus 1200 of the second embodiment, driving force of the second driving motor 1250 is transmitted to the arm 112 through the second transmitting/buffering unit 134 including the second crank shaft 1243 that rotates through a driving force of the second driving motor 1250 and the second crank rod 1242 that is coupled with the second crank shaft 1243 and rotates through rotation of the second crank shaft 1243, thereby extending and retracting the arm 112. As a result, even if a sudden change occurs in the driving force of the second driving motor 1250, the arm 112 can be extended and retracted without generating vibrations or impact shocks associated with a sudden change in extending speed or a sudden change in inertial load with respect to the arm 112.

In the dispensing apparatus 1200 according to the second embodiment, operation can be such that the second crank pin 1244 that couples the second crank lever 1241 with the second crank rod 1242 is rotated to a position corresponding to the predetermined discharge position from a position corresponding to the predetermined cleaning position through a driving force of the second driving motor 1250, i.e., the inverse of the operation of the second transmission/buffering unit 1240 explained with reference to FIGS. 15 to 17. In this case as well, the arm 112 can be retracted without vibration or impact shock.

As explained above, according to the dispensing apparatus of the present invention, driving force of the driving motor 120 is transmitted to the dispensing arm 110 through the transmission/buffering unit 180 including the crank shaft 184 that rotates through a driving force of the driving motor 120 and the crank rod 182 that is coupled with the crank shaft 184 and rotates through rotation of the crank shaft 184, thereby rotating the dispensing arm 110. As a result, the dispensing arm 110 can be rotated without generating vibrations or impact shocks in the dispensing arm 110. Therefore, the dispensing nozzle 143 can be carried to the predetermined discharge position without dispersing the reagent 152 drawn by the dispensing nozzle 143. As a result, precision when dispensing the reagent 152 can be improved.

According to the dispensing apparatus of the present invention, the syringe pump unit 141 is arranged on the dispensing arm shaft 111, thereby enabling a reduction in the installation area of the dispensing apparatus and a decrease in the size of the dispensing apparatus 100. The length of the syringe pump pipe 142 can be reduced, and a metal material can be used for a part of or for the entire the syringe pump pipe 142 in some cases. As a result, a reduction in pressure transmitted to the dispensing nozzle 143 or an increase in transmission time of a pressure that occur with vibrations or extension of the syringe pump pipe 142 can be avoided, thereby improving dispensing accuracy (an accuracy in the drawing amount of the reagent 152 and an accuracy in the discharge amount of the reagent 152) of the dispensing apparatus 100 and reducing dispensing time.

According to the dispensing apparatus of the present invention, since the transmission/buffering unit 180 that can increase a driving torque of the driving motor 120 is adopted, even if a heavy load (the syringe pump unit 141 having a weight of, for example, 400 grams) is mounted on the dispensing arm 110 and the weight of the dispensing arm 110 increases, the dispensing arm 110 can be rotated with a small driving force without affecting variations in the rotational speed or in the inertial load of the dispensing arm 110. Therefore, the driving motor 120 can be small or have low power consumption.

According to the dispensing apparatus of the present invention, even when the structure where the arm 112 is extended and retracted, and the cleaning device 1210 cleans the dispensing nozzle 143 is adopted, the arm 112 can be extended and retracted without generating vibrations or impact shocks associated with a sudden change in extending speed or a sudden change in inertial load with respect to the arm 112 by extending and retracting the arm 112 through the second transmission/buffering unit 1240 through a driving force of the second driving motor 1250.

INDUSTRIAL APPLICABILITY

As explained above, the dispensing apparatus according to the present invention can be utilized for auto analysis in clinical tests carried out at, for example, a hospital or a clinical examination institute and is suitable for, for example, improving precision when dispensing a reagent with respect to a specimen.

The invention claimed is:

1. A dispensing apparatus comprising:
   a dispensing arm that is rotatable, includes a drawing-and-discharging unit held at a distal end, and conveys a fluid drawn by the drawing-and-discharging unit at a predetermined drawing position to a predetermined discharge position;
   a driving motor;
   a driving transmission unit having a drive shaft, a driving pulley and a driving belt, the driving pulley is rotatably coupled to the to the dispensing arm by the driving belt; and
   a transmission/buffering unit having a crank shaft, a crank rod, a crank rod slider that is rotatable and has a through hole in which one end of the crank rod is inserted and fitted, and a crank lever that is rotatably coupled at one end with the driving motor and the other end is coupled to the crank rod through a crank pin, the crank rod has one end slidably inserted and fitted in the through hole of the crank rod slider and another end is coupled to the crank pin, the crank rod rotates around a rotating axis of the crank rod slider to rotate the crank rod slider;
   wherein the acceleration of the dispensing arm is gradual when the dispensing arm starts rotating from the predetermined drawing position and deceleration of the dispensing arm is gradual when the dispensing arm stops at the predetermined discharge position.

2. The dispensing apparatus according to claim 1, wherein the drawing-and-discharging unit includes a nozzle that draws and discharges the fluid, and is mounted on the dispensing arm.

3. The dispensing apparatus according to claim 1, further comprising an extending-and-retracting unit that extends and retracts the dispensing arm to move the drawing-and-discharge unit in a direction parallel to a length of the dispensing arm.

4. The dispensing apparatus according to claim 3, wherein the extending-and-retracting unit includes:
   a second driving motor that extends and retracts the dispensing arm; and
   a second transmission unit that includes a second crank shaft that rotates through a driving force of the second driving motor, and a second crank rod that is coupled with the second crank shaft and rotates with a rotation of the second crank shaft to extend and retract the dispensing arm.

5. The dispensing apparatus according to claim 4, wherein the second crank shaft and the second crank rod are coupled such that acceleration of the dispensing arm is gradual when the dispensing arm starts extending or retracting, and deceleration of the dispensing man is gradual when the dispensing arm stops extending or retracting.

6. The dispensing apparatus according to claim 4, wherein the second transmission unit further includes:
- a second crank lever that is coupled with the second crank shaft and rotates with a rotation of the second crank shaft; and
- a second crank rod that has one end coupled to the second crank lever through the second crank pin and another end coupled with the dispensing arm through a piston pin, and rotates around the piston pin to extend and retract the dispensing arm.

* * * * *